(12) United States Patent
Beadle et al.

(10) Patent No.: US 8,524,046 B2
(45) Date of Patent: Sep. 3, 2013

(54) DISTILLATION COLUMN PRESSURE CONTROL

(75) Inventors: Bruce R. Beadle, Kildeer, IL (US); Jason L. Noe, Mount Prospect, IL (US); Sara A. Williams, Des Plaines, IL (US)

(73) Assignee: UOP LLC, Des Plaines, IL (US)

(*) Notice: Subject to any disclaimer, the term of this patent is extended or adjusted under 35 U.S.C. 154(b) by 623 days.

(21) Appl. No.: 12/750,207

(22) Filed: Mar. 30, 2010

(65) Prior Publication Data
US 2011/0240525 A1 Oct. 6, 2011

(51) Int. Cl.
*B01D 3/42* (2006.01)
(52) U.S. Cl.
USPC ................... 203/1; 203/21; 203/91
(58) Field of Classification Search
USPC ............. 203/1, 91, 21; 196/111; 208/100, 208/308
See application file for complete search history.

(56) References Cited

U.S. PATENT DOCUMENTS

| | | | |
|---|---|---|---|
| 3,422,006 A | 1/1969 | Broughton | |
| 3,488,282 A | 1/1970 | Mitchell et al. | |
| 3,723,256 A | 3/1973 | Thompson | |
| 3,763,037 A | 10/1973 | Thompson | |
| 4,054,613 A | 10/1977 | Haskell et al. | |
| 4,090,923 A | 5/1978 | Haskell et al. | |
| 4,440,601 A * | 4/1984 | Katz et al. | 203/24 |
| 5,310,480 A | 5/1994 | Vidueira | |
| 6,245,956 B1 | 6/2001 | Hovis et al. | |
| 6,564,580 B2 * | 5/2003 | Bowen et al. | 62/623 |
| 7,078,580 B2 * | 7/2006 | Tian et al. | 585/833 |
| 7,267,746 B1 * | 9/2007 | Harris et al. | 202/160 |
| 8,282,816 B2 * | 10/2012 | Noe | 208/313 |

FOREIGN PATENT DOCUMENTS

| | | | |
|---|---|---|---|
| GB | 1392735 A1 | | 4/1975 |
| GB | 2163741 A | | 3/1986 |
| JP | 09-029001 | * | 2/1997 |
| JP | 09029001 A | | 2/1997 |

OTHER PUBLICATIONS

Lei, Z. et al., "Process improvement on separating C4 by extractive distillation," Chemical Engineering Journal. 85 (2/3): 379-386 (2002).
Saxena, A.C. et al., "Reducing energy use in extractive distillation," Energy Process. CAN. Northern Star Communications, (ISSN 0319-5759) 78(4):12-14 (Mar.-Apr. 1986).

* cited by examiner

*Primary Examiner* — Nina Bhat
(74) *Attorney, Agent, or Firm* — Mark R Willis

(57) ABSTRACT

Methods and systems for controlling the pressure of distillation columns, for example those operating under vacuum pressure and conventionally equipped with a steam ejector system, are described. Representative distillation columns are used in the separation of thermally unstable components, such as the physical solvent sulfolane, having relatively low volatility. Such columns are employed in aromatic hydrocarbon extraction processes for the recovery of purified $C_6$-$C_8$ aromatic hydrocarbons from a hydrocarbon feed stream (e.g., obtained from the catalytic reforming of naphtha).

20 Claims, 1 Drawing Sheet

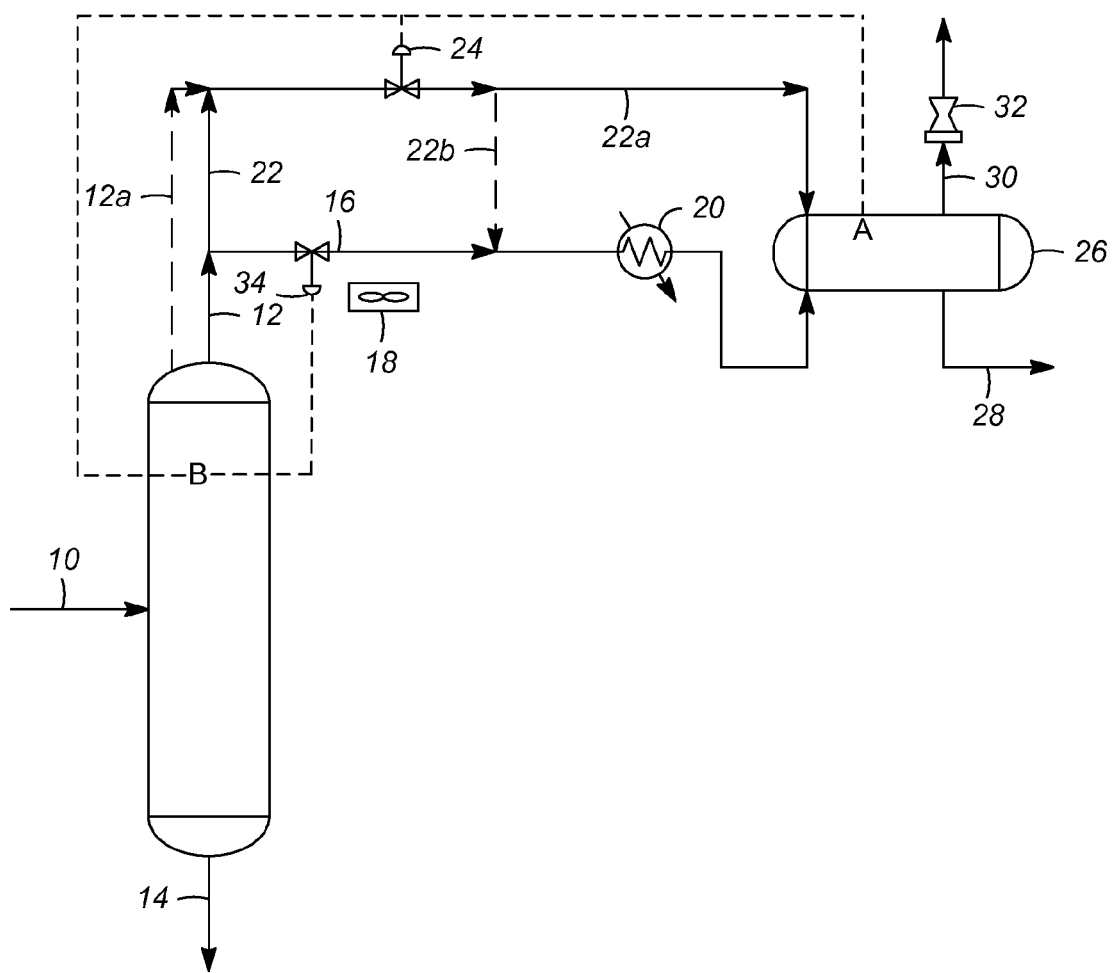

DISTILLATION COLUMN PRESSURE CONTROL

FIELD OF THE INVENTION

The present invention relates to pressure control in distillation column operations, and particularly those using vacuum pressures. A representative example is in the separation of a physical solvent that is subject to thermal degradation, such as sulfolane, from $C_6$-$C_8$ aromatic hydrocarbons.

DESCRIPTION OF RELATED ART

Distillation processes separate components of a mixture based on differences in their relative volatility. Such processes are widely employed in industry, and especially in petroleum refining and petrochemical production. Distillation generally involves contacting a rising vapor with a falling liquid, normally in a vertically elongated column to achieve multiple theoretical equilibrium stages of vapor-liquid contacting. Contacting and mass transfer efficiency are improved, and the length of column needed to achieve a theoretical equilibrium contacting stage is decreased, by incorporating contacting devices such as trays or packing materials in the column, numerous varieties of which are well known in the art.

As long as the formation of an azeotropic mixture is avoided within the column, the vapor becomes progressively enriched in the more volatile component(s) in the upward direction, while the liquid becomes progressively enriched in the less volatile component(s) in the downward direction. Distillation is therefore useful, for example, in separating hydrocarbons into fractions containing individual compounds having a similar relative volatility or boiling point. These fractions include crude oil-derived products of petroleum refining and petrochemical processing, such as naphtha, diesel fuel, LPG, and polymers. In some cases, distillation is used to separate specific compounds from a given impure mixture, for example containing other compounds of the same chemical or functional class, such as alcohols, ethers, alkylaromatics, monomers, solvents, inorganic compounds, etc.

Heat input is required to generate the necessary vapor fractions at successive stages and drive the distillation process. However, heating can be detrimental to some components that, while being desirably separated using distillation, exhibit thermal instability by undergoing degradation, decomposition, polymerization, etc. In some cases, therefore, it is especially important to carry out distillation at the lowest possible temperatures and consequently the lowest possible, but economically feasible, distillation column pressures. Vacuum distillation (or distillation at an absolute pressure below atmospheric pressure) is often selected for the separation of one or more thermally unstable components. Vacuum pressure in a column can be reliably maintained and controlled using steam ejectors as described, for example, by Hage, H., "Steam Ejector Fundamentals," JULY 1998 CHEMICAL PROCESSING, including the use of multistaged ejectors with intercondensers between stages. In the case of vacuum distillation operations processing high-boiling or highly condensable components, a source of a non-condensable component such as nitrogen may be introduced to the steam ejector system to facilitate pressure control, as described, for example, by Lines, J. R., "Lessons from the Field—Ejector Systems," HYDROCARBON ENGINEERING (1999). The use of such a control scheme, however, results in losses of some of the overhead product, or distillate, through entrainment in the nitrogen effluent. Additionally, this effluent stream often requires treatment to comply with emission and/or safety standards.

Particular vacuum distillation operations of interest include those used in the separation of high-boiling physical solvents from a desired product that is selectively dissolved in these solvents. Physical solvents, as opposed to chemical solvents such as amines, do not react chemically with the selectively dissolved product but instead promote its physical absorption based on a high equilibrium solubility at its partial pressure in an impure mixture (i.e., a higher Henry's law constant), relative to impurities in the mixture. Distillation of the physical solvent/selectively dissolved product mixture therefore allows recovery of both the product in a purified form and a "lean" physical solvent, essentially free of the product. The recovered physical solvent can then be reused in an extraction stage for selectively dissolving additional amounts of the desired product.

A particular process using sulfolane (i.e., tetrahydrothiophene dioxide, also known as tetramethylene sulfone) as a physical solvent to extract or selectively dissolve a $C_6$-$C_8$ aromatic hydrocarbon product from various hydrocarbon feedstocks including catalytic reformate, hydrogenated pyrolysis gasoline, coke-oven light oil, etc. is the UOP Sulfolane® Process as described by Meyers, R. A., "Handbook of Petroleum Refining Processes," The McGraw-Hill Companies, Inc. (2004), pp. 2.13-2.23. This reference illustrates two process flow schemes, one utilizing separate extraction and stripping stages, and another combining these stages into a single extractive distillation column Both types of Sulfolane processes include a recovery column for separating the $C_6$-$C_8$ aromatic hydrocarbon product from the physical solvent, sulfolane. Typically, this recovery column is operated under vacuum pressure to minimize thermal degradation of the solvent, as discussed above. A multistage steam ejector system with the introduction of nitrogen as a non-condensable material, is often used to control the vacuum pressure in this solvent recovery column.

A major consideration in the design and operation of aromatic extraction processes such as those described above is the energy cost. In commercial practice, the amount of energy required may be on the order of 1390-2100 kj/kg (600-900 BTU/lb) of aromatic hydrocarbon produced. For a typical operating unit producing about 300 kMTA (6,000 BPD) of $C_6$-$C_8$ aromatic hydrocarbons (i.e., benzene, toluene, and xylenes), the energy costs, namely steam, electric power, and cooling water, can account for over 80% of total operating costs. In contrast, solvent make-up costs are generally less than 5%, while labor/maintenance costs are typically 10%-20%. Any reduction in processing costs, and particularly energy costs, therefore, result in a significant economic advantage.

SUMMARY OF THE INVENTION

Aspects of present invention are associated with the discovery of methods for controlling the pressure of distillation columns, and especially those operating under vacuum pressure that are conventionally equipped with a steam ejector system as discussed above. Representative distillation columns are those used in the separation of thermally unstable components having relatively low volatility (e.g., a boiling point above 150° C. (302° F.)). Particular components include physical solvents used in the extractive separation of hydrocarbons such as aromatics, as well as polymer intermediates (e.g., nitriles) that are purified using distillation but polymerize at elevated temperatures. The physical solvent sulfolane, for example, is subject to oxidative thermal degradation, especially at the higher temperatures (e.g., the reboiler temperature) used in the bottom section of a distillation column In $C_6$-$C_8$ aromatic hydrocarbon extraction processes, this solvent is recovered by vacuum distillation from the aromatic hydrocarbon product, which is withdrawn as a vapor fraction from the upper section (e.g., above the top contacting tray) of the distillation column, generally referred to as the solvent recovery column The vapor fraction is then condensed to provide an aromatic hydrocarbon product liquid having a high content of $C_6$-$C_8$ aromatic hydrocarbons.

Importantly, distillation column pressure may be conveniently controlled by bypassing, with a part of the vapor fraction withdrawn from an upper section of the column (e.g., removed from the distillation column overhead above a top contacting stage), the cooler that is normally used to cool and/or condense this vapor fraction. This part of the vapor fraction serves as a "hot vapor bypass" that, prior to entering an overhead receiver vessel, has a significantly higher temperature relative to another part of the vapor fraction that passes through the cooler and then to the overhead receiver in the normal manner. The elevated vapor pressure of the hot vapor bypass allows the column pressure to be maintained at a desired value, typically below atmospheric pressure but still above the vapor pressure of the condensed liquid in the overhead receiver (the overhead product liquid). Advantageously, the flow of the hot vapor bypass can be controlled to control a vacuum pressure within the column (e.g., using a cascade control loop with a measured pressure, relative to a setpoint pressure, in turn generating a flow setpoint for the hot vapor bypass).

Accordingly, embodiments of the invention relate to methods for controlling pressure in a distillation column The methods comprise cooling and condensing, with a cooler, a first part of a vapor fraction (e.g., the net column overhead vapor) that is removed from the distillation column (e.g., in an upper section of the column). The cooler, and often a combination of coolers (heat exchangers), is therefore used to condense a portion of the first part of the vapor fraction removed from the column The methods further comprise controlling a flow of a second part of the vapor fraction. The second part bypasses the cooler, or bypasses one or more of a combination of the coolers (heat exchangers), to control the pressure. Normally, both the first part of the vapor fraction, after cooling and condensing it, and the second part of the vapor fraction (or hot vapor bypass) are introduced into an overhead receiver vessel.

Particular embodiments of the invention relate to methods for purifying aromatic hydrocarbons (e.g., aromatic extraction processes) in a hydrocarbon feed stream. The methods comprise selectively dissolving the aromatic hydrocarbons in a lean solvent (e.g., by contacting the lean solvent with the hydrocarbon feed stream in a countercurrent extraction or extractive distillation zone) to provide a rich solvent comprising dissolved hydrocarbons that are enriched in the aromatic hydrocarbons (relative to the hydrocarbon feed stream). The methods further comprise distilling the rich solvent in a distillation column (e.g., a vacuum distillation column), optionally after subjecting the rich solvent to stripping to remove low boiling (relative to the aromatic hydrocarbons) hydrocarbon contaminants. Distilling of the rich solvent comprises removing, from an upper section of the column, a vapor fraction (e.g., the net column overhead vapor) that is enriched (relative to the rich solvent feed to the column) in the aromatic hydrocarbons. A first part of the vapor fraction is cooled and condensed with a cooler. The flow of a second part of the vapor fraction is controlled to control a pressure of the column The pressure being controlled may be, for example, in the overhead receiver or otherwise at or above a top vapor-liquid contacting stage of the distillation column.

Further embodiments of the invention are directed to pressure control systems for distillation columns The systems comprise removal lines (e.g., conduits such as pipes) for first and second vapor fractions, where the lines are in fluid communication both an upper section of the distillation column and an overhead receiver. The systems further comprise at least one indirect heat exchanger (e.g., a fin fan heat exchanger and/or a shell and tube heat exchanger) having a process side in fluid communication with the first vapor fraction removal line and being disposed between the distillation column and the overhead receiver. A flow controller (e.g., flow control valve) regulates a flow through the second vapor fraction removal line, from the upper section of the distillation column to the overhead receiver, which bypasses the indirect heat exchanger. This flow is regulated in response to a measurement of pressure in the distillation column.

A number of important commercial advantages are associated with pressure control methods and systems according to the present invention. In particular, the requirement for high pressure steam in the steam ejector, normally in fluid communication with a vapor outlet of the overhead receiver of the distillation column, can be reduced or even eliminated. This is a substantial benefit, in view of unsuccessful attempts by refiners to reduce high utility costs by suspending the use of the steam ejectors (e.g., by blocking or isolating this equipment), particularly in aromatic hydrocarbon recovery processes. Invariably, when the ejectors are removed from service, the vacuum column pressure is essentially governed by the vapor pressure of condensed liquid in the overhead receiver. This pressure is not controlled and subject to variations with varying overhead product liquid compositions. Moreover, operating at this pressure, since it is often substantially lower than the column design pressure, can lead to an excessive volume of vapor flow through the column that ultimately results in vapor flooding and reduced column capacity.

In addition to energy (steam) costs associated with reducing or eliminating the operation of the steam ejector(s) conventionally used to induce and control a vacuum pressure, one or more associated process effluents may also be reduced or eliminated. In particular, the requirements for treatment of wastewater, and optionally a nitrogen effluent, generated from the steam ejector system, can be diminished. The wastewater results from condensing of steam used to drive the ejector(s) and the nitrogen effluent results from the nitrogen input to maintain a flow of non-condensables for conventional pressure control. Both of these streams are contaminated to some extent with components (e.g., $C_6$-$C_8$ aromatic hydrocarbons) present in the overhead vapor of the vacuum distillation column According to other embodiments, the steam ejector(s) may be used only discontinuously during the operation of the distillation column, for example during startup and/or at other discreet times when evacuation of non-condensable vapors from the column is desired. In any event, even with discontinuous use, utility costs and treatment costs for generated wastewater and waste gas are realized. The use of pressure control methods described herein therefore provide reliable control of pressure in the sub-atmospheric (vacuum) range. The methods thereby offer a number of significant benefits associated with vacuum distillation operations and in many cases a convenient alternative to steam ejector systems.

These and other aspects and features relating to the present invention are apparent from the following Detailed Description.

BRIEF DESCRIPTION OF THE DRAWING

The FIGURE depicts a representative vacuum distillation column that may be operated according to methods and with control systems as described herein.

The FIGURE is to be understood to present an illustration of the invention and/or principles involved. Details including some of the equipment (e.g., the reboiler) and some of the instrumentation and control loops, as well as other items not essential to the understanding of the invention are not shown. The broken lines 12a and 22b are intended to represent methods according to additional embodiments of the invention, but it will also be readily apparent to one of skill in the art having knowledge of the present disclosure that methods and systems for controlling distillation column pressure according to various other embodiments of the invention, will have configurations and components determined, in part, by the specific application.

DETAILED DESCRIPTION

As discussed above, the methods described herein relate to the control of pressure in distillation columns and particularly those operating under vacuum pressure, which is often desired in the separation by distillation of an overhead, vapor fraction having a bubble point (or temperature at which the first bubble of vapor forms at atmospheric pressure) that is well above the temperature usually achieved by cooling of this overhead vapor fraction with industrial cooling water. The bubble point of the vapor fraction is therefore generally above about 50° C. (122° F.), typically above about 100° C. (212° F.), and often above about 150° C. (302° F.)). In the case of distillation to achieve an overhead vapor fraction comprising substantially all (e.g., greater than 99%) of a single component or compound then these temperature ranges apply to the boiling point of that compound. Representative vacuum distillation operations may also be characterized in that one or more of the components in the mixture fed to the column is thermally unstable, meaning that it is susceptible to significant oxidation, degradation, decomposition, polymerization, etc. at elevated temperatures and particularly the highest temperatures that would be obtained in the bottom section (e.g., the reboiler), if the distillation column were operated at atmospheric pressure or above. In the case of sulfolane, for example, a commercially prohibitive, oxidative thermal decomposition rate is encountered at its normal boiling point of 285° C. (545° F.). However, a significantly lower bottom column temperature, for example in the range from about 165° C. (329° F.) to about 205° C. (401° F.), is typically achieved using vacuum distillation.

Particular, non-limiting, vacuum distillation operations include those used in the separation of a hydrocarbon product, as a more volatile fraction of a feed stream to the distillation column, from a physical solvent, as a less volatile fraction of the feed stream. Physical solvents include those used to selectively extract or dissolve desired hydrocarbon products of interest, in an upstream extraction or extractive distillation zone. For example, a hydrocarbon product comprising $C_6$-$C_8$ aromatic hydrocarbons (benzene, toluene, and mixed xylene isomers (ortho-, meta-, and para-xylene)) may be recovered from an impure mixture of hydrocarbons in a hydrocarbon feed stream (e.g., comprising a catalytic reformate, hydrogenated pyrolysis gasoline, and/or coke-oven light oil) by extraction, or otherwise extractive distillation, into a physical solvent comprising sulfolane (i.e., tetrahydrothiophene dioxide, also known as tetramethylene sulfone) as discussed above. Other representative physical solvents include propylene carbonate, tributyl phosphate, and methanol. Still others include alkyl- and alkanol-substituted heterocyclic hydrocarbons such as alkanolpyridines (e.g., 3-(pyridin-4-yl)-propan-1-ol) and alkylpyrrolidones (e.g., n-methyl pyrrolidone), as well as dialkylethers of polyethylene glycol (e.g., polyethylene glycol dimethyl ether). Separation of the physical solvent, for reuse in the extraction or extractive distillation of the desired hydrocarbons, occurs in a solvent recovery column that typically operates under vacuum pressure to minimize oxidative degradation and/or other types of thermal decomposition of the physical solvent.

A representative distillation column illustrating various aspects of the invention is shown in the FIGURE. The distillation column may be, for example, a typical solvent recovery column, as discussed above, operating under vacuum pressure. A feed stream 10 comprising first and second fractions to be separated is passed to column 100. The first fraction may be, for example, the more volatile vapor fraction 12 (or combination of 12 and 12a) removed from the upper section (e.g., above a top contacting tray (not shown) or above internal packing material (not shown)) of the column 100 and therefore having a lower bubble point than the second fraction, which may be the less volatile liquid fraction 14 removed from the lower section (e.g., below a bottom contacting tray (not shown) or below internal packing material (not shown)) of the column 100. The first and second fractions may independently comprise substantially a single component or compound, in which case the bubble point of the fraction is substantially the boiling point of that component or compound. According to a representative embodiment directed to a solvent recovery column in an aromatic hydrocarbon extraction process, the first fraction may comprise a mixture of components, and particularly a mixture of $C_6$-$C_8$ aromatic hydrocarbons, which may be present in a combined amount generally greater than about 95%, and often greater than about 99%, by weight of the fraction. The second fraction may comprise substantially (e.g., greater than about 99% by weight) the physical solvent (e.g., sulfolane).

The feed stream 10 passing to column 100 therefore comprises at least a first, more volatile component or compound having a relatively low boiling point and a second, less volatile component or compound having a relatively high boiling point. The vapor fraction 12 is therefore enriched in the first component, relative to feed stream 10, while the liquid fraction 14 is enriched in the second component, relative to feed stream 10. In a representative embodiment directed to an aromatic hydrocarbon extraction process in which the column 100 is a solvent recovery column, therefore, the first component may be sulfolane and the second component may be selected from $C_6$-$C_8$ aromatic hydrocarbons. According to some embodiments, vapor fraction 12 of distillation column 100 may be removed as, and therefore comprise, more than one stream exiting the upper section of this column As shown in the FIGURE, for example, the vapor fraction may be a combination of 12 and 12a, shown with a broken line, taken from different points in the upper section of column 100. It is also understood that feed stream 10 may be composed of a number of separate streams (not shown) passing to column 100, optionally at different locations (heights or tray numbers) along the column It is further understood that other vapor and liquid or combined vapor/liquid fractions (not shown) may be removed from column 100, optionally at different locations.

According to embodiments of the invention, a first part 16 of vapor fraction 12 is passed through coolers 18, 20. As illustrated in the FIGURE, coolers 18, 20 may be, respectively, a first indirect heat exchanger 18 (e.g., a fin fan cooler)

using air as a cooling medium and a second indirect heat exchanger 20 (e.g., a trim condenser) using water as a cooling medium. First part 16 of vapor fraction 12 is therefore cooled and condensed after removal from column 100. The condensing of first part 16 of vapor fraction 12 generally refers to at least a portion of this part being condensed to liquid that is at equilibrium with its vapor (after passing through cooler 20) at approximately cooling water temperature, typically from about 25° C. (77° F.) to about 45° C. (113° F.). The condensed liquid, together with additional liquid condensed in the overhead receiver 26 from second part 22 (or 12a) of vapor fraction 12 (or combination of 12 and 12a), optionally after passing through cooler 20 (via broken line 22b), is recovered as overhead product liquid 28, for example an aromatic hydrocarbon product liquid having a content of $C_6$-$C_8$ aromatic hydrocarbons in excess of 99% by weight. These aromatic hydrocarbons are often separated by downstream distillation into fractions enriched in benzene, toluene, and xylenes (relative to the aromatic hydrocarbon product liquid) with the latter often being further separated and isomerized to recover and purify desired xylene isomers (e.g., para-xylene for the production of purified terepthalic acid (PTA)). Product liquid 28 refers to the net overhead liquid removed from column 100, and in many cases a significant amount of the total liquid flow to overhead receiver 26 is returned to column 100 as reflux (not shown).

The flow of a second part 22 (or 12a) of vapor fraction 12 (or combination of 12 and 12a) is controlled using a controller such as hot vapor bypass control valve 24 and this flow bypasses both of the coolers 18, 20, as shown with line 22a, or according to alternative embodiments, only the first cooler 18, as shown with broken line 22b. In either case, the bypassing of at least one of coolers 18, 20 results in second part 22 (or 12a) of vapor fraction 12 (e.g., at hot vapor bypass control valve 24 and immediately upstream of overhead receiver 26), to be hotter than first part 16 of vapor fraction 12, after passing through coolers 18, 20. For example, while this temperature of first part 16 after cooling may approximate industrial cooling water temperature as discussed above, the temperature of second part 22 may approximate a top temperature in column 100, having a representative range, in the case of a solvent recovery column in an aromatic hydrocarbon extraction process, from about 75° C. (167° F.) to about 100° C. (212° F.). According to a representative embodiment, the cooler first part 16 of vapor fraction 12, after cooling and condensing, is introduced into overhead receiver 26 at a location below that at which second part 22 (or 12a) is introduced, through 22a, as illustrated in the FIGURE. This particular routing of the cooler and hotter parts of the vapor fraction allows a temperature gradient to form in the liquid condensed in overhead receiver 26, minimizing disturbances from excessive condensation at the top of this vessel.

Second part 22 (or 12a) of vapor fraction 12 is therefore a hot vapor bypass, having a vapor pressure above that of condensed liquid in overhead receiver 26. Both of these vapor pressures may be below atmospheric pressure, or otherwise the vapor pressure of the hot vapor bypass may be above atmospheric pressure while the vapor pressure of the condensed liquid, and consequently the vapor pressure of the first part 16 of vapor fraction 12 after cooling, is below atmospheric pressure. In any event, the vapor pressure of the hot vapor bypass is equal to or above a setpoint pressure, for example controlled in the vapor space of overhead receiver 26 at point A. This pressure control point corresponds to that associated with the conventional operation of steam ejector 32, which, during its operation, is in fluid communication with a vapor outlet 30 of overhead receiver 26. An alternative setpoint pressure is controlled in an upper section of column 100 at point B. A representative setpoint pressure is from about 0.1 bar (1.5 psi) to about 1 bar (14.5 psi), corresponding to the operating pressure of column 100.

As discussed above, the hot vapor bypass advantageously provides effective pressure control without relying on continual operation of steam ejector 32, thereby saving significant utility and waste stream treatment costs. In particular, the equal or higher vapor pressure of the hot vapor bypass, relative to that of the setpoint pressure, allows hot vapor bypass control valve 24 to control this setpoint pressure by controlling the flow of second part 22 (or 12a) of vapor fraction 12 in response to a measured pressure (e.g., at point A), or deviation between the setpoint pressure and measured pressure, in column 100 or in its overhead receiver 26. According to one control scheme, the measured pressure, relative to the pressure setpoint, is used as a basis for a percentage opening or a flow setpoint for the hot vapor bypass, namely the second part 22 (or 12a) of vapor fraction 12, through hot vapor bypass control valve 24. In an alternative control scheme, a measured differential pressure (e.g., the differential pressure between points A and B) is used as a basis for a valve opening percentage or a flow setpoint for the hot vapor bypass. In yet another embodiment, hot vapor bypass control valve 24, having a percentage opening or a flow setpoint based on a differential pressure, operates in conjunction with main vapor control valve 34, prior to (upstream of) first indirect heat exchanger 18 (e.g., a fin fan cooler). Main vapor flow control valve 34 may have a flow setpoint based on a measured pressure, for example at point B. The combination of differential pressure control, using hot vapor bypass control valve 24 and pressure control, using main vapor control valve 34, therefore serves to maintain a desired pressure in column 100, even without the use of steam ejector 32.

Particular embodiments of the invention relate to the use of the column pressure control methods, as described herein, in an aromatic hydrocarbon extraction process. Accordingly, aspects of the invention are associated with methods for separating or purifying $C_6$-$C_8$ aromatic hydrocarbons from an impure hydrocarbon feed stream (i.e., having a lower content of $C_6$-$C_8$ aromatic hydrocarbons compared to a $C_6$-$C_8$ aromatic hydrocarbon product liquid stream obtained from the process). The methods comprise selectively dissolving the aromatic hydrocarbons in a lean solvent to provide a rich solvent comprising dissolved hydrocarbons that are enriched in the aromatic hydrocarbons (relative to the hydrocarbon feed stream) due to the selectivity of the solvent for these hydrocarbons. Contact between the lean solvent and the hydrocarbon feed stream is normally performed in a countercurrent extraction zone or a countercurrent extractive distillation zone, with the rich solvent liquid exiting the bottom of an extraction or extractive distillation column The rich solvent, optionally after being subjected to stripping, is then distilled in a solvent recovery column According to aspects of the invention, the pressure of this column may be controlled under vacuum pressure according to the methods discussed above. As noted, a particular process of interest involves the purification of $C_6$-$C_8$ aromatic hydrocarbons, obtained from the catalytic reforming of naphtha (e.g., from the overhead of the reformate splitter) using sulfolane as the selective solvent.

Overall, aspects of the invention are associated with processes and systems for controlling the pressure of distillation columns, and particularly those operating under vacuum pressure such as solvent recovery columns used in aromatic hydrocarbon extraction processes. Those having skill in the art, with the knowledge gained from the present disclosure, will recognize that various changes could be made in the above processes and systems without departing from the scope of the present disclosure. Mechanisms used to explain theoretical or observed phenomena or results, shall be interpreted as illustrative only and not limiting in any way the scope of the appended claims.

The invention claimed is:

1. A method for controlling pressure in a distillation column operating at sub-atmospheric pressure, the method comprising:
   (a) cooling and condensing a first part of a vapor fraction, removed from the distillation column, with a cooler; and
   (b) controlling a flow of a second part of the vapor fraction, bypassing the cooler, to control the pressure,
      wherein the vapor fraction removed from the distillation column is enriched in a second component that is more volatile that a first component present in the distillation column, and the first component is a physical solvent.

2. The method of claim 1, further comprising introducing (i) the first part of the vapor fraction, after cooling and condensing it, and (ii) the second part of the vapor fraction, into an overhead receiver vessel.

3. The method of claim 2, wherein (i) is introduced to the overhead receiver at a location below that at which (ii) is introduced.

4. The method of claim 1, wherein the cooler is a first indirect heat exchanger using air as a cooling medium, and wherein, in step (b), the flow of the second part of the vapor fraction bypasses the first indirect heat exchanger.

5. The method of claim 4, wherein, in step (b), the flow of the second part of the vapor fraction bypasses both the first indirect heat exchanger and a second indirect heat exchanger using water as a cooling medium.

6. The method of claim 1, wherein the vapor pressure of the first part of the vapor fraction, after cooling and condensing it in step (a), is below atmospheric pressure.

7. The method of claim 1, wherein a flow control valve controls the flow of the second part of the vapor fraction in response to a measured pressure, relative to a setpoint pressure, in the distillation column or in an overhead receiver of the distillation column.

8. The method of claim 7, wherein the measured pressure is in a vapor space in the overhead receiver of the distillation column.

9. The method of claim 8, wherein the setpoint pressure is from about 0.1 bar (1.5 psi) to about 1 bar (14.5 psi).

10. The method of claim 1, wherein the first part of the vapor fraction is cooled in step (a) to a temperature from about 25° C. (77° F.) to about 45° C. (113° F.).

11. The method of claim 1, wherein the second component is selected from $C_6$-$C_8$ aromatic hydrocarbons and the first component is tetrahydrothiophene dioxide.

12. A method for controlling pressure in a distillation column operating at sub-atmospheric pressure, the method comprising:
   (a) cooling and condensing a first part of a vapor fraction, removed from the distillation column, with a cooler, wherein the first part of the vapor fraction is cooled to a temperature from about 25° C. (77° F.) to about 45° C. (113° F.); and
   (b) controlling a flow of a second part of the vapor fraction, bypassing the cooler, to control the pressure.

13. The method of claim 12, further comprising introducing (a) the first part of the vapor fraction, after cooling and condensing it, and (b) the second part of the vapor fraction, into an overhead receiver vessel.

14. The method of claim 12, wherein the cooler is a first indirect heat exchanger using air as a cooling medium, and wherein, in step (b), the flow of the second part of the vapor fraction bypasses the first indirect heat exchanger.

15. The method of claim 14, wherein, in step (b), the flow of the second part of the vapor fraction bypasses both the first indirect heat exchanger and a second indirect heat exchanger using water as a cooling medium.

16. The method of claim 13, wherein the vapor pressure of the first part of the vapor fraction, after cooling and condensing it in step (a), is below atmospheric pressure.

17. A method for controlling pressure in a distillation column operating at sub-atmospheric pressure, the method comprising:
   (a) cooling and condensing a first part of a vapor fraction, removed from the distillation column, with a cooler; and
   (b) controlling a flow of a second part of the vapor fraction, bypassing the cooler, to control the pressure;
   wherein a flow control valve controls the flow of the second part of the vapor fraction in response to a measured pressure, relative to a setpoint pressure, in the distillation column or in an overhead receiver of the distillation column, wherein the measured pressure is in a vapor space in the overhead receiver of the distillation column and the setpoint pressure is from about 0.1 bar (1.5 psi) to about 1 bar (14.5 psi).

18. The method of claim 17, further comprising introducing (i) the first part of the vapor fraction, after cooling and condensing it, and (ii) the second part of the vapor fraction, into an overhead receiver vessel.

19. The method of claim 17, wherein the cooler is a first indirect heat exchanger using air as a cooling medium, and wherein, in step (b), the flow of the second part of the vapor fraction bypasses the first indirect heat exchanger.

20. The method of claim 17, wherein the vapor pressure of the first part of the vapor fraction, after cooling and condensing it in step (a), is below atmospheric pressure.

* * * * *